(12) United States Patent
Wong et al.

(10) Patent No.: US 10,902,193 B2
(45) Date of Patent: Jan. 26, 2021

(54) AUTOMATED GENERATION OF WEB FORMS USING FILLABLE ELECTRONIC DOCUMENTS

(71) Applicant: Think Research Corporation, Toronto (CA)

(72) Inventors: Alfred Kuo Hui Wong, Toronto (CA); Laith Azer, Toronto (CA)

(73) Assignee: Think Research Corporation, Toronto (CA)

( * ) Notice: Subject to any disclaimer, the term of this patent is extended or adjusted under 35 U.S.C. 154(b) by 0 days.

(21) Appl. No.: 15/840,733

(22) Filed: Dec. 13, 2017

(65) Prior Publication Data
US 2019/0179885 A1    Jun. 13, 2019

(51) Int. Cl.
| | |
|---|---|
| *G06F 17/00* | (2019.01) |
| *G06F 40/174* | (2020.01) |
| *G06F 40/106* | (2020.01) |
| *G06F 40/154* | (2020.01) |
| *G06F 40/186* | (2020.01) |
| *G16H 20/60* | (2018.01) |
| *G16H 10/60* | (2018.01) |
| *G16H 30/20* | (2018.01) |

(52) U.S. Cl.
CPC .......... *G06F 40/174* (2020.01); *G06F 40/106* (2020.01); *G06F 40/154* (2020.01); *G06F 40/186* (2020.01); *G16H 10/60* (2018.01); *G16H 20/60* (2018.01); *G16H 30/20* (2018.01)

(58) Field of Classification Search
None
See application file for complete search history.

(56) References Cited

U.S. PATENT DOCUMENTS

| | | | |
|---|---|---|---|
| 8,812,946 B1 | 8/2014 | Kopylov et al. | |
| 2002/0111961 A1* | 8/2002 | Billings | G06F 17/211 715/221 |
| 2007/0180148 A1 | 8/2007 | Yadidian | |
| 2008/0021920 A1* | 1/2008 | Shapiro | G06F 16/447 |
| 2012/0063684 A1 | 3/2012 | Denoue et al. | |
| 2014/0223277 A1 | 8/2014 | Kimber et al. | |
| 2015/0339268 A1 | 11/2015 | Bednarz, Jr. et al. | |

OTHER PUBLICATIONS

European Patent Office, Extended European Search Report for EP Patent App. No. 18212097.2, dated May 15, 2019.

* cited by examiner

*Primary Examiner* — Mustafa A Amin
(74) *Attorney, Agent, or Firm* — Own Innovation; James W. Hinton

(57) ABSTRACT

Many forms exist as fillable electronic documents (FEDs), such as in the Portable Document Format (PDF). Generating web-based forms that match these FEDs, even with existing software tools, is time consuming and laborious. A computing system and a related process are provided that automatically and very quickly generate a web-based form that looks the same as a FED. In particular, the computing process includes extracting a fillable object (e.g. a checkbox) in a FED and generating a pixel image of an entire page in the FED. A web-fillable object (e.g. a JSON fillable object) is generated that corresponds to the fillable object. The web-based form is created by overlaying the web-fillable object over the pixel image.

20 Claims, 20 Drawing Sheets

```
1  module Services
2    module PointToPixelHelper
3      PDF_POINTS_TO_AN_INCH = 72
4
5      def compute_pixels(point, target_dpi)
6        return 0 if point <= 0.0 || target_dpi <= 0.0
7
8        (point / PDF_POINTS_TO_AN_INCH) * target_dpi
9      end
10    end
11  end
```

```
template_file = File.read("test/output/templates/form.liquid")
template = Liquid::Template.parse(template_file)

File.open("test/output/index.html", "wb") do |f|
    f.write template.render('page_width' => 2550,
        'page_height' => 3300,
        'scaling_factor' => 0.4,
        'pages' => pages_json,
        'input_fields_by_page' => input_fields_by_page)
end
rescue => e
    puts 'ERROR ****************'
    puts e
    puts 'ERROR ****************'
end
end
end
```

```
def self.build_top_left_point(j_field, page_pixel_height, target_dpi = 300)
  pp_helper = TempPointToPixelHelper.new point = { x: 0, y: 0 }
  j_rectangle = extract_field_rectangle_j_field if j_rectangle
    point[:x] = pp_helper.compute_pixels(j_rectangle.lower_left_x, target_dpi)
    upper_right_y_in_px = pp_helper.compute_pixels(j_rectangle.upper_right_y, target_dpi)
    point[:y] = page_pixel_height - upper_right_y_in_px
  end point
end
```

( C-2 )

```
def self.build_bottom_right_point(j_field, page_pixel_height, target_dpi = 300)
  pp_helper = TempPointToPixelHelper.new point = { x: 0, y: 0 }
  j_rectangle = extract_field_rectangle_j_field if j_rectangle
    point[:x] = pp_helper.compute_pixels(j_rectangle.upper_right_x, target_dpi)
    lower_left_y_in_px = pp_helper.compute_pixels(j_rectangle.lower_left_y, target_dpi)
    point[:y] = page_pixel_height - lower_left_y_in_px
  end point
end
```

Figure 15

```
module Eform
  class GetPdfParseJson < BaseInteractor
    DEFAULT_PARSED_PDF_DPI = 112.94
    DEFAULT_PARSED_PDF_WIDTH = 960
    DEFAULT_PARSED_PDF_HEIGHT = 1242 def call
      validate_required_params :alice_id, :route, :pdf_bytes, :current_user_name
      context[:parsed_pdf_response] = get_parsed_pdf_response(context.pdf_bytes)
    end private def get_parsed_pdf_response(pdf_bytes)
      pdf_parser_client = Services::PdfParser::Client.new
      pdf_parser_client.translate_pdf(pdf_bytes, DEFAULT_PARSED_PDF_DPI, DEFAULT_PARSED_PDF_WIDTH, DEFAULT_PARSED_PDF_HEIGHT)
    rescue Services::FDRestClient::Error => e
      context.fail! message: e.message
    end
  end
end
```

AUTOMATED GENERATION OF WEB FORMS USING FILLABLE ELECTRONIC DOCUMENTS

TECHNICAL FIELD

The following relates to electronic document processing, and more particularly to computing systems and processes that automatically use a fillable electronic document to generate a corresponding web form.

DESCRIPTION OF THE RELATED ART

Fillable electronic documents (FEDs) are electronic documents that have portions of their document purposely specified to be filled in by another party, whether automatically or manually by a person. These portions that are to be fillable could, for example, be a checkbox, a radio button to be selected or unselected, a line to receive data (e.g. text, numbers, alphanumeric data, an electronic signature, etc.), and a box to receive data (e.g. text, numbers, alphanumeric data, an electronic signature, etc.). A non-limiting example data format of a FED is Portable Document Format (PDF).

These FEDs can be printed out onto paper and a person can fill in the fillable portions using a pen, pencil, or the like. Alternatively, a person can use a computing program adapted to the specific data format of the FED to fill in the fillable portions of the FED.

Fillable electronic documents are very common. On the other hand, it is herein recognized that web-based data is becoming ubiquitous as this type of data is readily accessible and viewable via Internet Browsers and web-enabled applications (e.g. commonly called apps). With the proliferation of mobile devices (e.g. smart phones, smart watches, tablets, desktop computers, laptops, and other web-enabled devices), web-based data formats are readily digitally communicable and readily able to be processed across the variety and volume of mobile devices. In an example embodiment, non-limiting examples of relatively common web-based data include HTML data, XML data, JSON data, JavaScript data, and the like.

People therefore desire to create a web-based fillable form that matches or is similar to the FED. This process typically includes a person that codes or programs a web-based fillable form to generate the same or similar text, images, and placement of the fillable portions. The person would also need to visually identify the style of the fonts and estimate the positioning of the text so as to create a similar look and feel of the FED. This process is labor intensive. To reduce the person's labor, the created web forms are sometimes made to look more simple compared to the FED. As a result, the web form does not match the FED. For example, a web form is made to look more like a conventional website or web page that continuously scrolls down, rather than a set of distinct pages of the FED.

Existing HTML form builders (e.g. available under the trade names MACCAW, WYSIWYG, Dream Weaver, etc.) provide software tools help a person to build a web form and to design websites. However, even with these HTML tools, the challenges for a technician (e.g. a coder, web developer, a person, etc.) remain in terms of inefficiency and time-consuming labor when creating a HTML form version of a FED (e.g. a PDF document, a Word Document, or the like).

Other software tools that help to generate and to render fillable PDF documents require a PDF rendering software in order for the computing device to display the PDF document and for a user to fill in the fillable portions of the PDF document. Furthermore, the computing systems that renders the fillable PDF document requires coding libraries specific to the PDF format to extract the values and the fields. However, this rendering software and these coding libraries may not be available on all computing devices or mobile devices. Therefore, it herein recognized that it is desirable to generate web-based data that are readily digitally communicable and readily able to be processed across the variety and volume of mobile devices.

It is herein recognized that the problem of creating the web forms becomes even more technically challenging as the complexity of the FED increases (e.g. lots of text, many images, chart and word formatting variation). The problem of creating the web forms also becomes even more technically challenging as the length of each FED increases (e.g. a document that has tens or hundreds of pages) and as the number of different FEDs increases (e.g. different forms for different purposes). It is further herein recognized that the problem also becomes even further technically challenging when scaling the computing process of generating web forms for many different computing devices and their users who, in turn, have so many different electronic documents.

It is therefore herein desired to address one or more of the above issues.

BRIEF DESCRIPTION OF THE DRAWINGS

Embodiments will now be described by way of example only with reference to the appended drawings wherein:

FIG. 12 is an example of computer executable instructions for converting point coordinates in a FED to pixel coordinates in a web form.

FIGS. 13a and 13b are an example of computer executable instructions for generating a fillable web form that looks like a FED.

FIGS. 14a and 14b are an example of computer executable instructions for reading in a FED into the binary content and to compute meta information about the FED, according to an example aspect of FIG. 13a.

FIG. 15 is an example of computer executable instructions for extracting the fillable portions of the FED and generating the corresponding fillable web objects for the web form, according to an example aspect of FIG. 14b.

FIG. 16 is an example of computer executable instructions for generating a web-based document according to a format for a software application by Think Research Corporation, called Form Designer.

FIGS. 17a and 17b are an example of computer executable instructions for computing floating component and child component fillable objects, according to an example aspect of FIG. 16.

DETAILED DESCRIPTION

Figure 1:
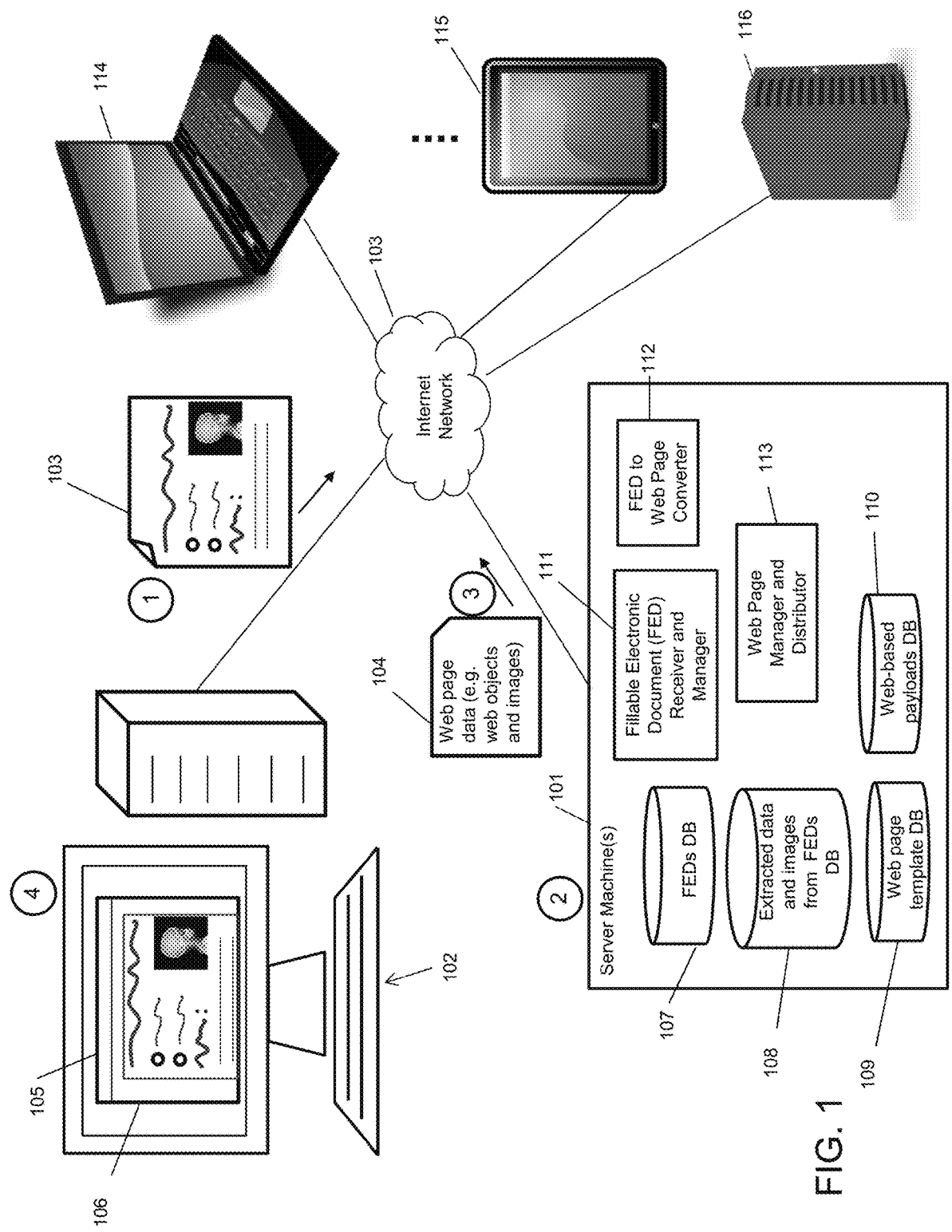
FIG. 1 is a schematic diagram of an example computing system for automatically generating web forms using fillable electronic documents (FEDs).

It will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures and components have not been described in detail so as not to obscure the example embodiments described herein. Also, the description is not to be considered as limiting the scope of the example embodiments described herein.

The examples described herein relate to a fillable electronic document (FED) that are in the PDF format. However, the principles described herein may be also applicable to converting other currently known and future known formats of FEDs into web-based fillable forms. For example, other FED formats that are applicable include those FEDs that store fillable field information and the positions of these fillable fields.

In an example embodiment, an application programming interface, or some other software, is used to interact with the given FED format to read the FED, such as to extract the position of the fillable fields.

The fillable portions in a FED, as well as the fillable objects in a web-based form, include, but are not limited to check boxes, radial buttons, number fields, text fields, and data fields that receive other types of data. Lines or boxes, or other visual indicators, could be used to visually show the data field. In an example embodiment, the fillable data is fillable by a person interacting with a computing device. In another example embodiment, the fillable data is fillable by the computing device itself or another computing device, as in the case of machine-to-machine communications. Non-limiting example types of data that could be filled into a fillable portion or a fillable object include: text, numbers, alphanumeric data, an electronic signature, an image, computer code, audio data, and biometric data. Non-limiting examples of biometric data include: finger print data, EKG data, MRI scanned data, images of medical scans from different modalities, and heart rate data. In an example embodiment, the computing device or the other computing device takes the JSON output and prefills values, whereby the server modifies the JSON value to have a "default value" field and then any other system can interpret and show that value.

It will be appreciated that while some of the examples used herein relate to health or medical information, the computing systems and the processes are applicable to any type of information. It is herein recognized that forms are used in many industries, organizations, and communities and are also used in personal situations.

In an example embodiment, a computing system automatically uses a FED to generate a web-based form that looks the same as the original FED, and which is completed very quickly (e.g. in the order of seconds or less). The process includes extracting the fillable portions of the FED and a pixel image of the FED. For example, the computing system automatically extracts all of the fillable fields located in a FED (e.g. height, width, x, y location, font, etc.). The computing system also generates a high resolution picture for each page of the FED. The process further includes the computing system then creating a web-based payload (e.g. in a JSON data format). For example, with all of the information extracted and the images of each page obtained, the computing system creates a model that represents all of this information so that any other computing system can use this information (called the web-based payload) to create a fillable web form. The process further includes using the web-based payload to create a fillable web form. For example, this payload can be used to automatically create a HTML document or can be used in other web-based tools to create a fillable web form, or combinations thereof.

In an example aspect, the computing system and the related process therefore convert a fillable PDF into a HTML fillable form that looks exactly the same in an automated way. The computing system and related process do not require a PDF renderer or a PDF viewer to display a fillable PDF. In another aspect, the fillable web forms are viewable and accessible on any device that that has a web interface (e.g. an Internet Browser or a web-enabled app).

Turning to FIG. 1, an example embodiment of a computing system is shown, including the flow of data between computing devices in the system. The system includes one or more server machines 101, also herein after called a server and a user device 102 that digitally communicates with the server 101 over a network 103, such as the Internet. In an example embodiment, the server 101 is configured to communicate with many user devices 114, 115 that may be of different types and makes. Examples of user devices include a laptop, a tablet, a desktop computer, a smart watch, a large screen display, a smart television, a video game console, and integrated devices between a display device and an input device (e.g. a projector or television in data communication with a smart phone or tablet). In another example embodiment, the server 101 communicates with a third party server 116 that sends the server 101 a FED or a batch of FEDs for batch conversion to web forms. In other words, the server 101 may interact with non-user devices to obtain one or more FEDs and to generate one or more web-fillable forms.

In an example process, at operation 1, the user device 102 transmits a FED 103 to the server 101, via the Internet. At operation 2, the server 101 automatically generates a web-based payload 104 that includes fillable web objects and one or more images that correspond to each page in the FED 103. In the example shown, the payload is formatted as web page data 104. At operation 3, the server 101 transmits this payload of web page data 104 to the user device 102 via the Internet. At operation 4, the user device 102 compiles the web page data 104 and displays the same in a web interface 106, such as an Internet Browser. The compiled web page data results in the display of a web form 105 that looks the same as the FED 103, and allows a user to fill in data just like the FED 103.

These example operations are, in an example embodiment, executed in parallel by the server 101 for many different devices 114, 115, 116 that request their FEDs to be converted to web forms.

Although a server 101 is shown, the server can include multiple server machines that communicate with other third party server machines (e.g. cloud servers). The functionality and the data of the server 101 can be distributed amongst these different server machines. The server 101 includes a FEDs database 107 that stores the FEDs to be converted to web-fillable forms. The server 101 further includes a database 108 that stores extracted data and images from the FEDs. The extracted data includes the position of the fillable portions in a given page of a given FED. The extracted data could also include the number of pages in the FED, the page format or sizing of the FED, the author of the FED, the owner of FED, a document identifier of the FED, the date of creation of the FED, the last date of modification of the FED, etc. This meta data of the FED could be also stored with the resulting web-based payload. The server 101 also includes a web page template database 109 that stores one or more web page templates. For example, each template has different CSS (Cascading Style Sheets) data. CSS describes how web elements (e.g. HTML elements) are to be displayed on screen or in other media. CSS can control the layout of multiple web pages all at once. The server 101 also includes a web-based payload database 110 that stores the web-based payloads. In another example, the further processed web pages or other web-based documents, that have been derived from the web-based payloads, are stored in the database 110 or in a separate database.

In another example embodiment, the server 101 does not have a FEDs database 107 or a web-based payload database 110. Instead, the server does not store the FED in a database, but processes a received FED on the fly. For example, the server 101 extracts and builds the web-based payload on the fly, and returns the same to a client device. During the on-the-fly processing, the server neither stores the web-based payload nor stores the FED.

Continuing with FIG. 1, the server 101 also includes a FED receiver and manager 111 that receives incoming FEDs to be converted. The FED receiver and manager module 111 stores the FEDs in the FEDs database 107. The server 101 also includes a FED-to-web page converter module 112 that automatically generates the web pages based on the FEDs. This module 112, for example, interacts with the databases 107, 108, 109 and 110. The server 101 also includes a web page manager and distributor module 113 that transmits the web page to external devices and external servers.

Figure 2:
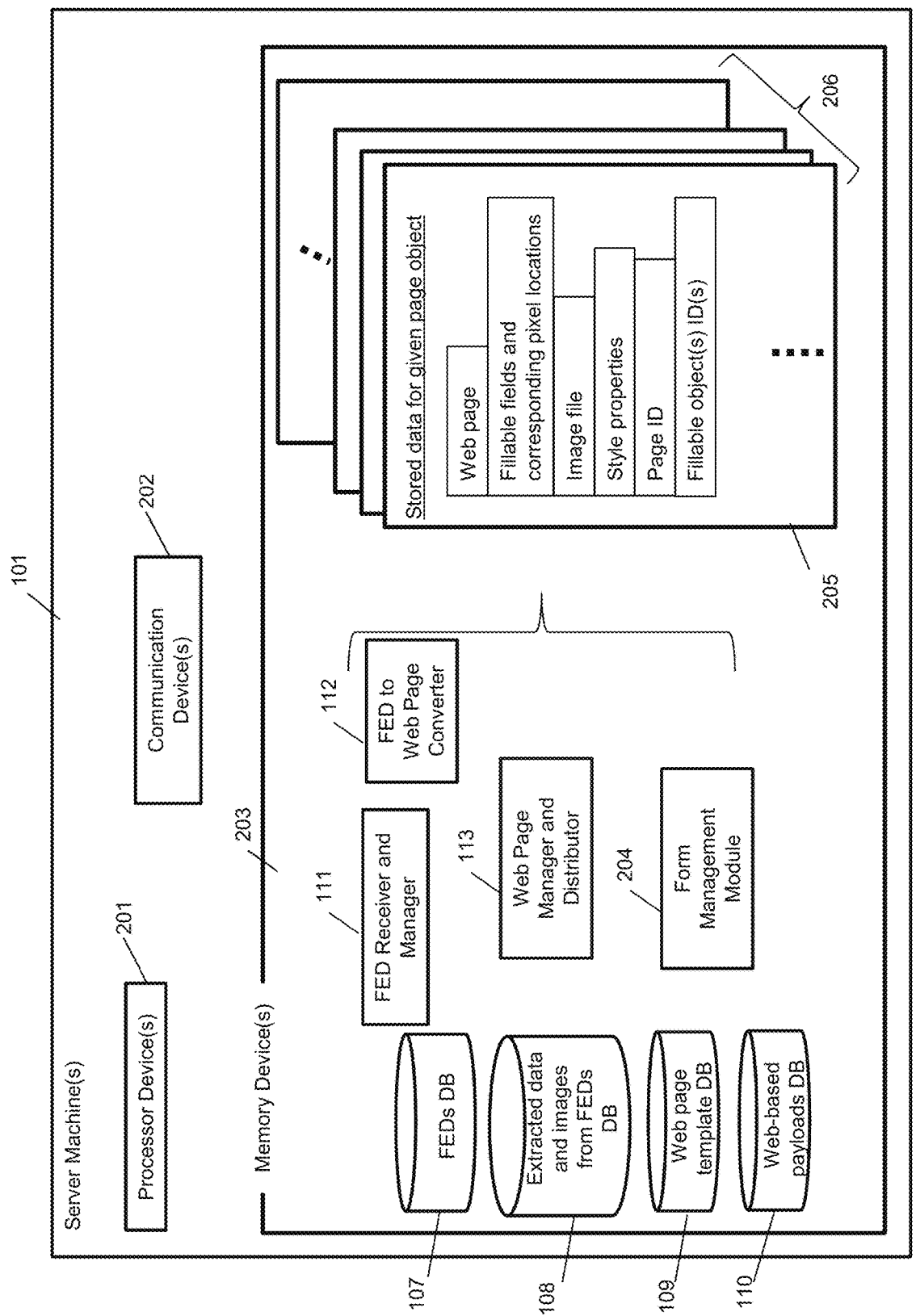
FIG. 2 is a schematic diagram of an example computing architecture of a server system including device components and data components stored in memory.

Turning to FIG. 2, a more detailed view of the components of the server 101 is shown. The server includes one or more processing devices 201. It also includes one or more communication devices 202 that transmit and receive data over the network 104. It also includes one or more memory devices 203.

These one or more memory devices 203 store the databases 107, 108, 109, and 110. The one or more memory devices also store modules 111, 112, and 113.

In another example embodiment, there is also a form management module 204 stored in memory 203 that includes software for designing web forms. For example, the web-based payloads are inputted into the module 204, and graphical user interface is provided in the module 204 to add further elements to the web form.

In an example embodiment, an example data representation of a web-based form 206, which has been generated from an FED, is outputted by the modules and stored in memory 203. The example form 206 includes multiple web pages and an example instance of such a page 205 is shown in FIG. 2. The example page 205 includes the web page itself, fillable fields and corresponding pixel locations, an image file, style properties, a page ID that identifies the given page 205, and fillable object IDs that identify the fillable objects in the given page 205. There may be other data associated with the given page 205.

Figure 3:
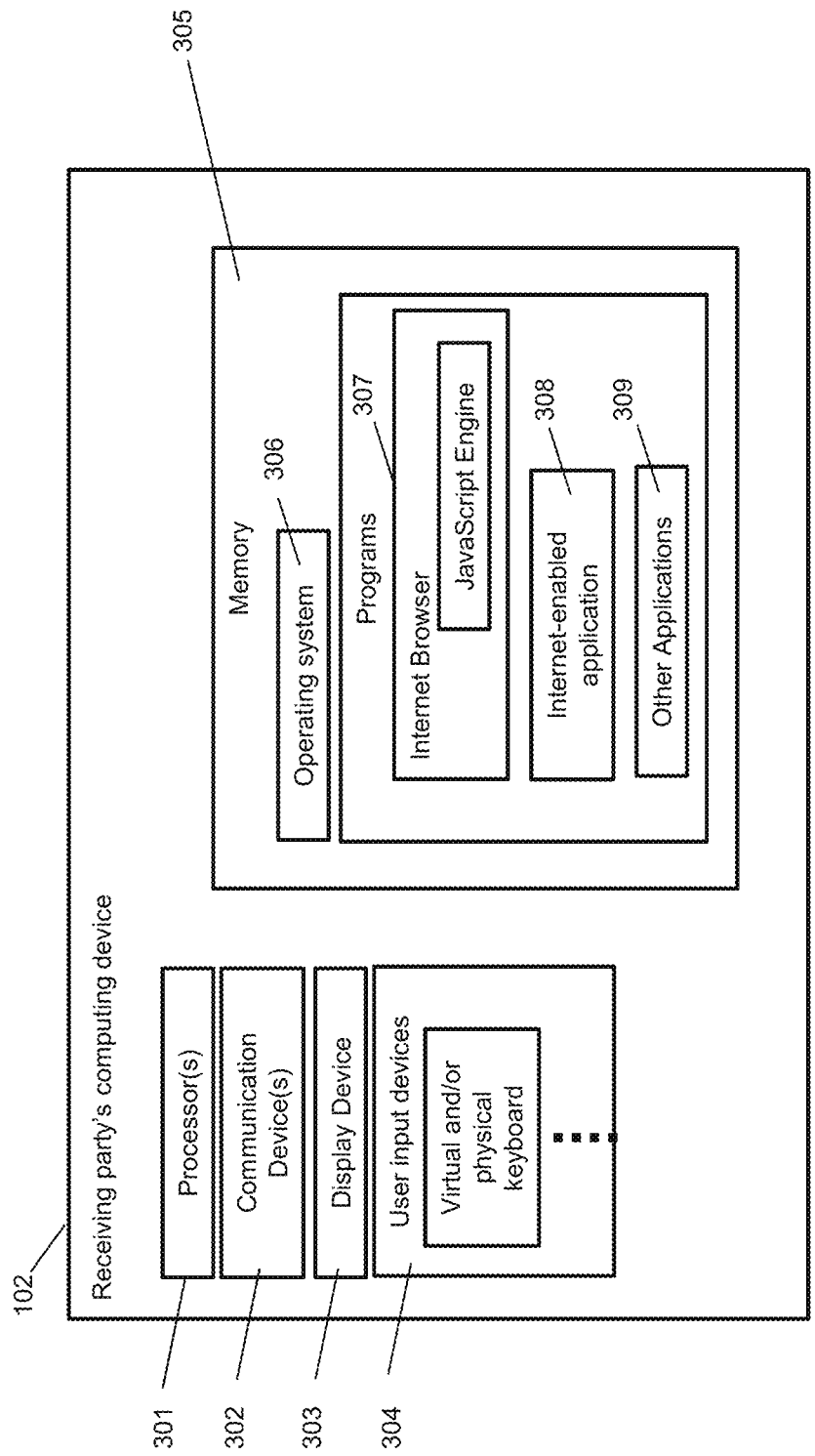
FIG. 3 is a schematic diagram of an example computing architecture of a receiving party's computing device including device components and data components stored in memory.

Turning to FIG. 3, an example of components of a receiving party's computing device (e.g. the second user device) 102 is shown. It includes one or more processors 301, one or more communication devices 302, a display device 303 or an audio device, or both, and one or more user input devices 304. The input devices 304 can include a physical keyboard or a virtual keyboard, or both. The input devices 304 can also include a pointing mechanism, such as a touch screen, touch surface, or a computer mouse. Other examples of currently known user input devices and user output devices are applicable. These input devices could be used by a user to input data into a fillable web form that has been generated by the server 101.

The device 102 also includes memory device(s) that store an operating system 306 and one or more programs 307, 308, 309 that operate within the operating system. For example, the Internet browser 307 is an example of a web application. An example structure of an Internet browser includes a user interface (UI) that interacts with a browser engine. The browser engine interacts with a rendering engine. The rendering engine in turn interacts with a networking module, a Java Script interpreter (or JavaScript engine), and a UI backend. The UI also interacts with the UI backend. The browser engine interacts with local data storage within the Internet browser.

An Internet-enabled application 308 (e.g. a dedicated FED to webpage converter application) is another example of a web application.

Figure 4A:
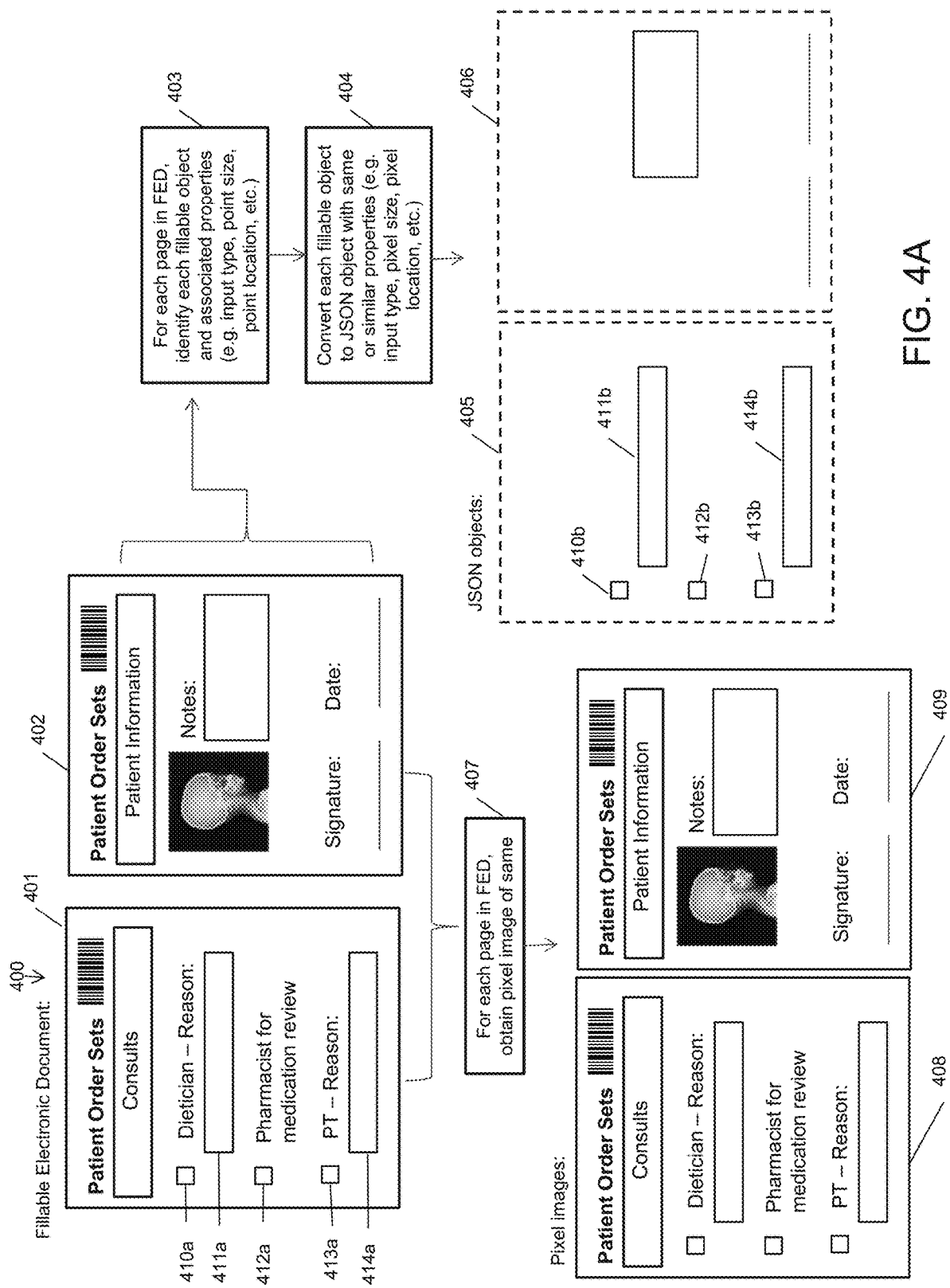
FIGS. 4A and 4B are a flow diagram of an example computing process for automatically using a FED to generate a web form.
Figure 4B:
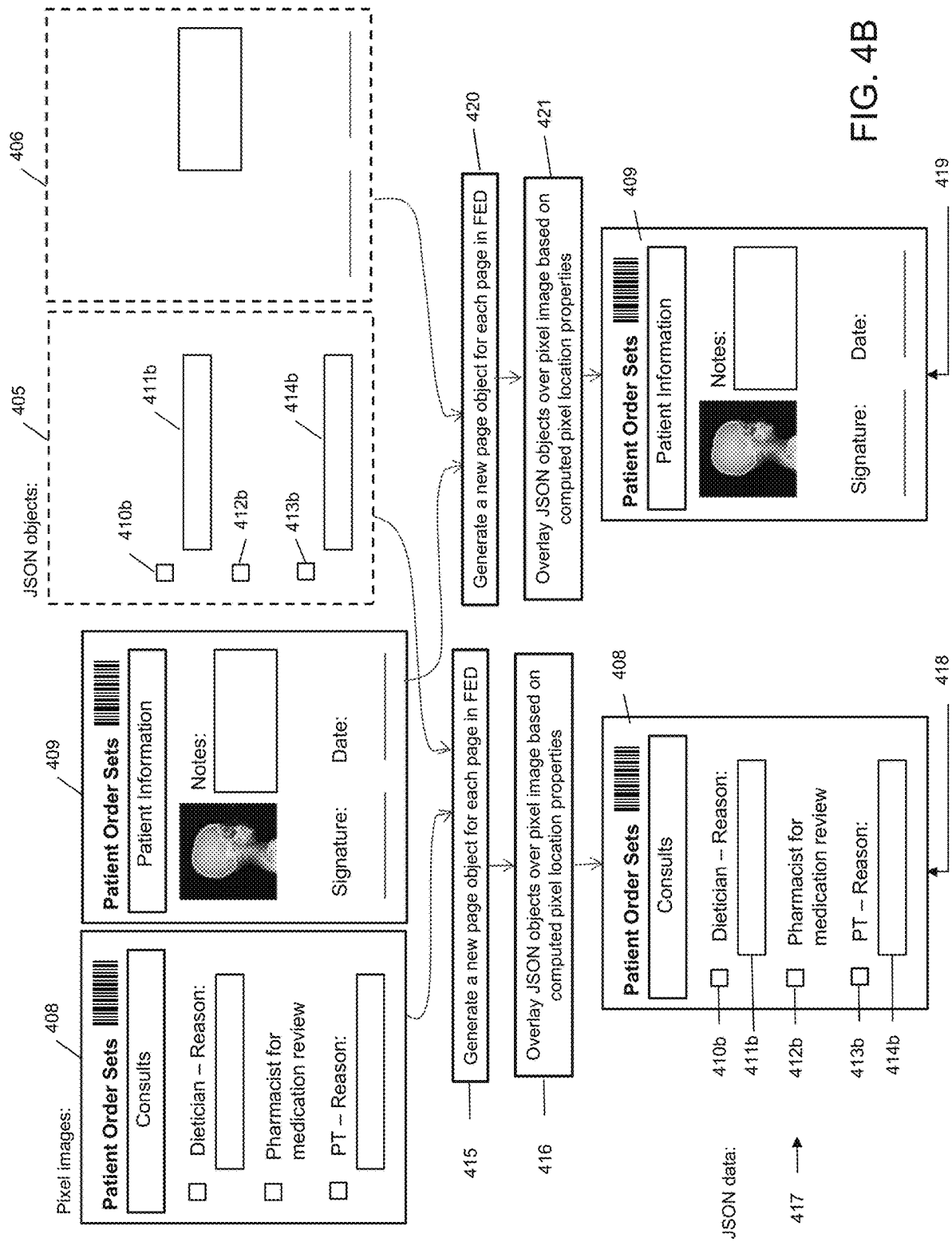

Turning to FIGS. 4A and 4B, an example computing process is provided for automatically generating web-based forms from a FED. An FED 400 is shown that includes two pages 401, 402. The pages, for example, are part of a PDF document and include text (e.g. headers, sub-titles, description, etc.) and images (e.g. a barcode, an image of a body scan, etc.). Each of these pages also include fillable portions. For example, page 401 includes fillable portions 410*a*, 411*a*, 412*a*, 413*a*, and 414*a*. The positions of these fillable portions are stored according to a positioning system specific to the FED format. For example, if the FED is a PDF document, the positioning system identifies objects based on a point system with an origin of (0,0) located on the top left corner of a page. Other FEDs could use other coordinate systems with a different positioned origin. This FED 400 is processed by the server 101.

In particular, at block 403, the server 101 processes each page by identifying each fillable object and the associated properties of the fillable object. These properties include, for example, the input type (e.g. check box, radial button, signature line, date field, general text field, some other data type, etc., the fillable object's size according to the point coordinate system, and the fillable object's location according to the point coordinate system. This information is, for example, stored in the format along with the FED and is a form of meta data of the FED. At block 404, the server 101 converts each fillable object to a JSON fillable field object with the same or similar properties. For example, these properties include the input type, the JSON field object's size according to the pixel coordinate system, and the JSON object's location according to the pixel coordinate system. For example, this results in JSON data representing one page 405 that includes the fillable field objects 410*b*, 411*b*, 412*b*, 413*b*, and 414*b*, which correspond to the fillable portions 410*a*, 411*a*, 412*a*, 413*a*, and 414*a*. Similarly, JSON data representing a second page 406 is generated that includes fillable field objects that correspond to the fillable portions in the page 402.

Although these JSON fillable field objects are illustrated as boxes in FIGS. 4A and 4B, in practice, these objects are strings of code. For example, below is an example format of code representing fillable field objects:

```
"input_fields": [
  {
    "x": 900,
    "y": 800,
    "width": 80,
    "height": 70,
    "type": "checkbox"
  },
  {
    "x": 985,
    "y": 800,
    "width": 80,
    "height": 70,
    "type": "text"
  },
  ...
]
```

In another aspect of the process, the server 101 obtains a pixel image of each of the pages 400, 401 (block 407). In particular, a pixel image 408 is outputted based on the entire page 401, and a pixel image 409 is outputted based on the entire page 402. In an example embodiment, the FED 400 is a PDF document which renders its images according to dots per inch (DPI), not according to pixels. Other ways of rendering images are used in different FED software. Therefore, the pixel image is a different data format from the images shown in a FED.

The generated pixel images could be in any of the currently known and future known data formats. Examples of currently known image formats include .png, .tiff, .jpeg, .gif, .bmp, etc.

At block 415, the server uses the pixel image 408 and the JSON data of the page 405 (including the fillable field objects 410*b*, 411*b*, 412*b*, 413*b*, and 414*b*) to generate a new web page. In particular, at block 415, the server generates a new page object corresponding to the page 401. At block 416, the server overlays the fillable field objects 410*b*, 411*b*, 412*b*, 413*b*, and 414*b* over the pixel image 408 based on the computed pixel location properties. This results in JSON data for a web-based page 418 that looks the same as the FED page 401.

This process is repeated using the pixel image 409 and the fillable field object data from the JSON page 406, according to the operations 420 and 421. These operations output the web-based page 419 that looks the same as the FED page 402.

Together, the web-based pages 419 and 419 are compiled to generate a web-based form 417 that looks equivalent to the FED 400.

Figure 5:
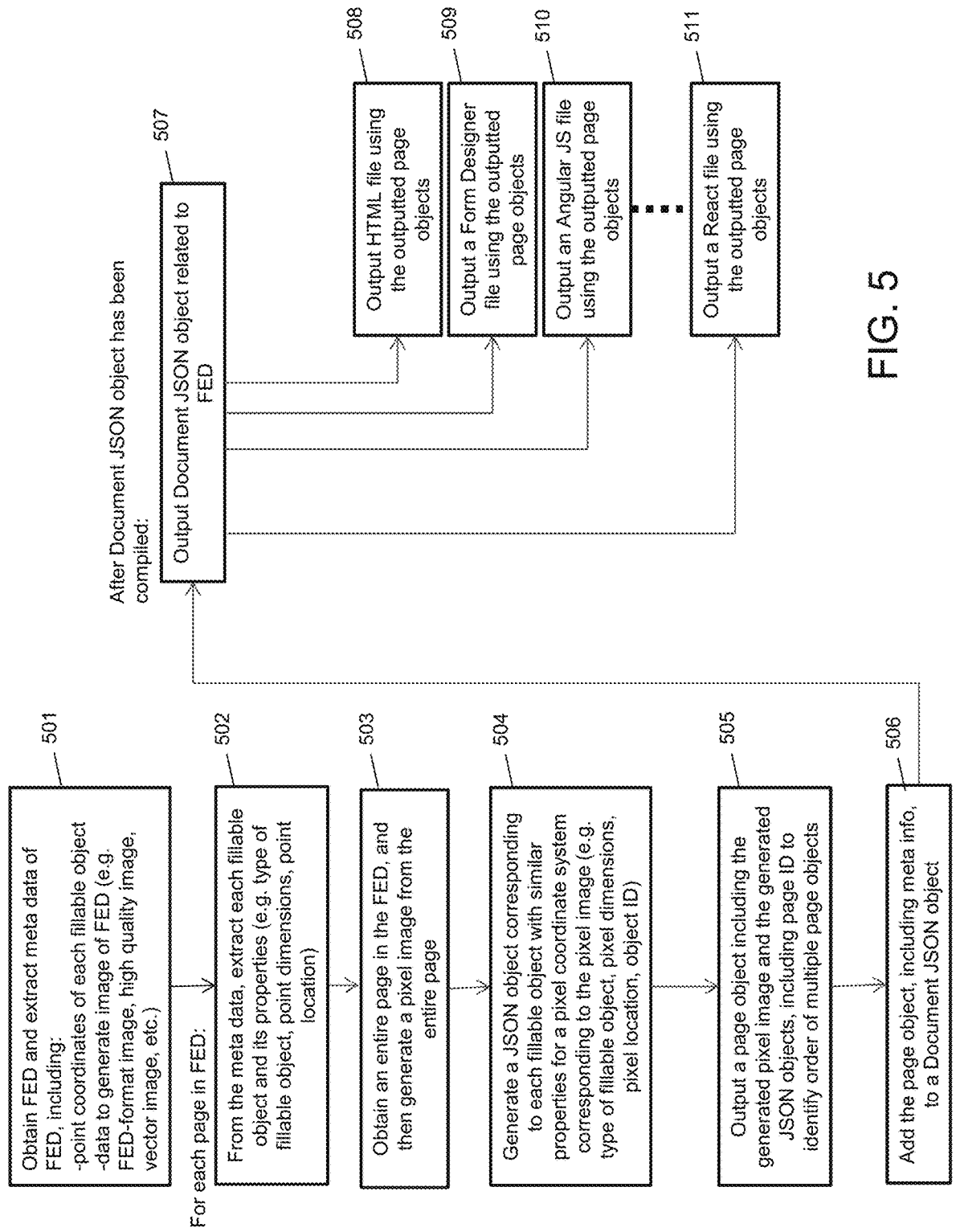
FIG. 5 is a flow diagram of example computer executable instructions for automatically generating a web form using a FED.

Turning to FIG. 5, example executable instructions are shown that are executed by the server 101 to automatically generate web-based form using a FED.

Block 501: The server obtains a FED and extracts meta data of the FED. The meta data includes: point coordinates of each fillable object or fillable portion in the FED, and data to generate an image of the FED (e.g. a high resolution image according to a FED format).

Then, for each page in the FED, the blocks 502 to 506 are executed.

Block 502: From the meta data, the server extracts each fillable object and its properties (e.g. type of fillable object, point dimensions, point location).

Block 503: Obtain an entire page in the FED, and then generate a pixel image from that entire page. In an example embodiment, this includes obtaining an image of the entire page in the FED and converting the image into a pixel image. In another example, the data of the entire page in the FED is sufficient to directly generate the pixel image.

Block 504: Generate a fillable field object within a page JSON object (e.g. the JSON fillable field object) corresponding to each fillable object with similar properties for a pixel coordinate system corresponding to the pixel image (e.g. type of fillable object, pixel dimensions, pixel location, object ID).

Block 505: Output the page JSON object including the generated pixel image and the generated JSON fillable field objects. In an example embodiment, a page ID is included with the page JSON object to identify order of the multiple page objects.

Block 506: Add the page JSON object, including the meta information, to a document JSON object.

After creating each web-based page object and adding each of these page JSON objects to the document JSON object, at block 507, the server outputs the document JSON object. This document JSON object includes web-based page objects that respectively correspond to the pages in the FED. This combined output, for example, forms the web-based payload.

This web-based payload can then be further processed in one or more several ways, either in the alternative or in combination. These outputs are described in blocks 508, 509, 510 and 511. In other words, a web-based payload could lead to one or several of these types of outputs.

Block 508 takes the web-based payload to output a HTML file.

Block 509 takes the web-based payload to output a form designer file, created using software provided by Think Research Corporation.

Block 510 takes the web-based payload to output an AngularJS file. AngularJS is a JavaScript-based front-end application.

Block 511 takes the web-based payload to output a React file. React is a JavaScript library for building user interfaces.

The web-based payload could also be used to form other formats of outputs.

It will be appreciated that the document JSON object, which is the web-based payload, is comprised of different sections. These different sections, for example, are page sections that are created and stored in this one object. So for example, the document JSON object could look something like this:

```
"document": {
    "pages": [
        {
            "page_num": 1,
            "base64_page_image":"<base64 encoded string>"
            "input_fields": [
                {
                    "x": 900,
                    "y": 800,
                    "width": 80,
                    "height": 70,
                    "type": "checkbox"
                },
                {
                    "x": 985,
                    "y": 800,
                    "width": 80,
                    "height": 70,
                    "type": "text"
                },
                ...
            ]
        },
        {
            "page_num": 2,
            "base64_page_image":"<base64 encoded string>"
            "input_fields": [
                {
                    "x": 900,
                    "y": 800,
                    "width": 80,
                    "height": 70,
                    "type": "checkbox"
                },
                {
                    "x": 985,
                    "y": 800,
                    "width": 80,
                    "height": 70,
                    "type": "text"
                },
                ...
            ]
        },
        ...
    ]
}
```

Figure 6:
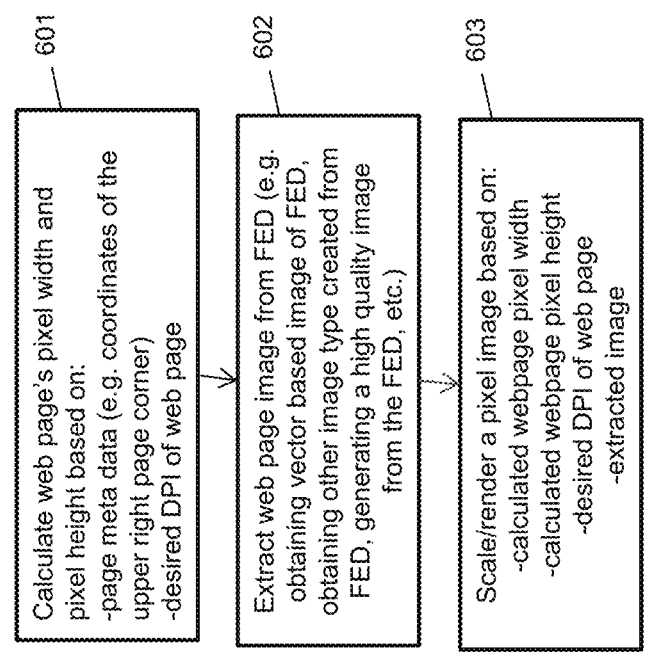
FIG. 6 is a flow diagram of example computer executable instructions for converting a vector image of an FED to a pixel image, according to an example aspect of an operation in FIG. 5.

Turning to FIG. 6, example executable instructions are provided for implementing block 503.

Block 601: The server 101 calculates the desired web page's pixel width and pixel height based on: page meta data (e.g. coordinates of the upper right page corner), and the desired DPI (Dots Per Inch) of the web page.

In an example embodiment, the desired DPI of the web page is a hard-coded value. In an example embodiment, the desired DPI is selected by a user who wishes to generate the web page version of a FED. For example, the user selects or inputs the desired DPI via a user interface. In another example, the desired DPI is automatically computed or selected by the server 101. For example, when a client device (e.g. 102, 114, 115) interacts with the server 101, it sends information about itself to the server. Examples of such information include: the type of device (e.g. mobile device or not), the make of the device (e.g. iPhone, etc.), the screen resolution of the device, and the viewing size of the web application (e.g. the Internet browser or the app). The DPI, for example, is also derived as a function of the desired data size of the pixel image. It is recognized that a higher DPI would lead to a larger data file.

Block 602: The server extracts an image of the web page from the entire FED page. This image is saved as pixel image. In an example embodiment, the pixel image is encoded as base64 encoded bytes. However, other types of encoding value could be used.

Block 603: The server scales or renders the pixel image based on data, including: calculated webpage pixel width; calculated webpage pixel height; desired DPI of web page; and the extracted image.

Figure 7:
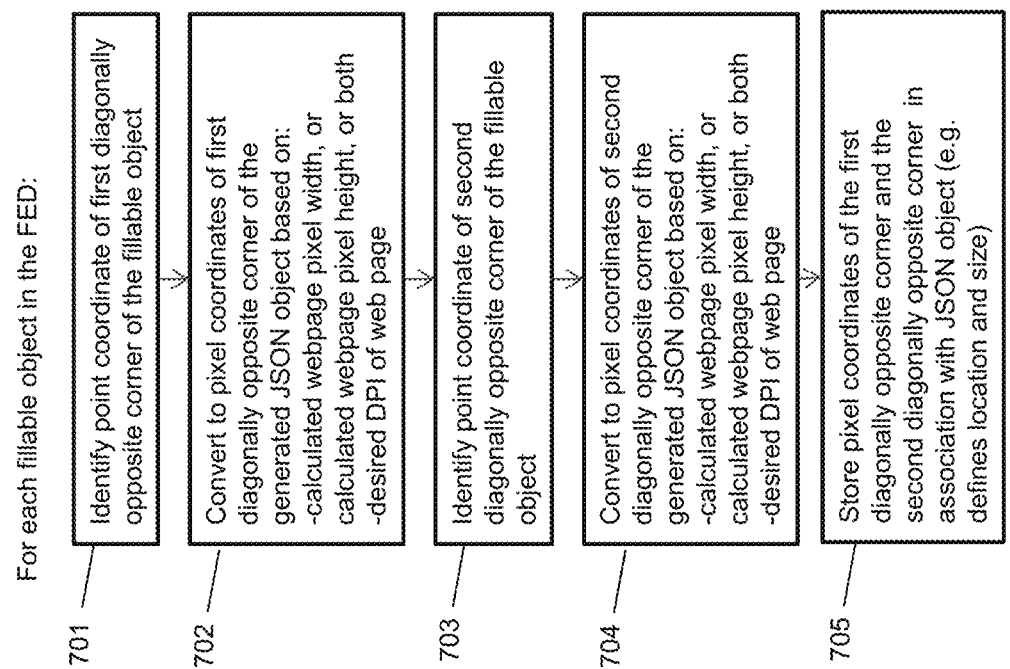
FIG. 7 is a flow diagram of example computer executable instructions for generating a fillable web object that corresponds to a fillable portion in a FED, according to an example aspect of an operation in FIG. 5.

Turning to FIG. 7, example executable instructions are provided for implementing block 504. These instructions are, for example, executed for each fillable object or fillable portion in a FED to determine the pixel positioning and sizing.

Block 701: The server 101 identifies a point coordinate of first diagonally opposite corner of the fillable object in the given FED page.

Block 702: The server converts the point coordinate of a first diagonally opposite corner to a pixel coordinate of a first diagonally opposite corner of the generated JSON object based on the data, including: calculated webpage pixel width, or calculated webpage pixel height, or both; and desired DPI of the web page.

Block 703: The server identifies a point coordinate of a second diagonally opposite corner of the fillable object in the given FED page.

Block 704: The server converts the point coordinate of the second diagonally opposite corner to a pixel coordinate of a second diagonally opposite corner of the generated JSON object based on data, including: calculated webpage pixel width, or calculated webpage pixel height, or both; and, desired DPI of web page.

Block 705: The server then stores the pixel coordinates of the first diagonally opposite corner and the second diagonally opposite corner in association with the JSON object. These pixel coordinates can be used to define the location and the size of the JSON fillable object.

Figure 8:
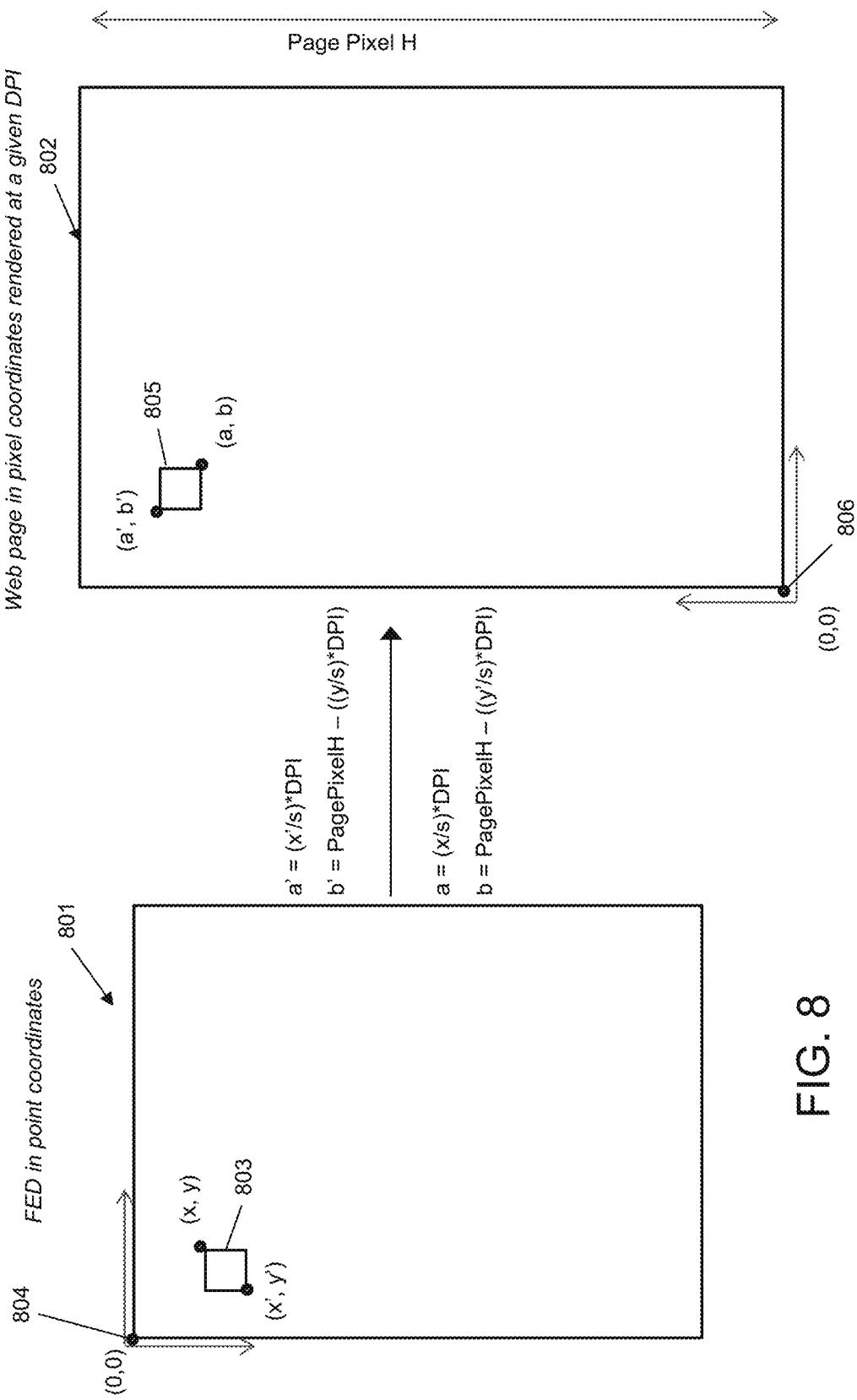
FIG. 8 is a schematic diagram of an example of computing the pixel coordinates of a fillable web object based on point coordinates of the corresponding fillable portion in the FED.

Turning to FIG. 8, an example schematic illustrates how a fillable object or fillable portion 803 on a FED page 801 is used to generate a JSON fillable object 805 on a web page 802. The FED page 801 uses point coordinates and has an origin (0,0) 804 that is located in the top right corner of the page 801. The web page 802 is dimensioned using a pixel coordinate system and has an origin (0,0) 806 located on the bottom right corner of the page 802. The web page's pixel height H, is also indicated in FIG. 8.

Regarding the fillable object or portion 803, it is a check box that has its opposite corners marked with coordinates. For example, the upper right corner has the points coordinates (x,y) and the lower left corner has the points coordinates (x', y'). These values, amongst others, are used by the server 101 to compute new coordinates for the JSON fillable object 805. To maintain the same "look", the relative dimensions and relative positioning of the object 805 in the page 802 is the same as the object 803 in the page 801.

In particular, the JSON fillable object 805 is defined by an upper left coordinate (a',b') in pixels and a lower right coordinate (a,b) in pixels. The computations, for example, include:

$$a'=(x'/s)*DPI$$

$$b'=PagePixelH-((y'/s)*DPI)$$

$$a=(x/s)*DPI$$

$$b=PagePixelH-((y'/s)*DPI)$$

s is a scaling constant. In an example embodiment, s is 72. However, other values could be used.

DPI is the desired dots per square inch.

PagePixelH is the calculated height of the resulting web page 802, defined in the number of pixels.

In an example aspect, the subtraction operations above are to accommodate for the different corners coordinates being provided by the point system of the FED.

Figure 9:
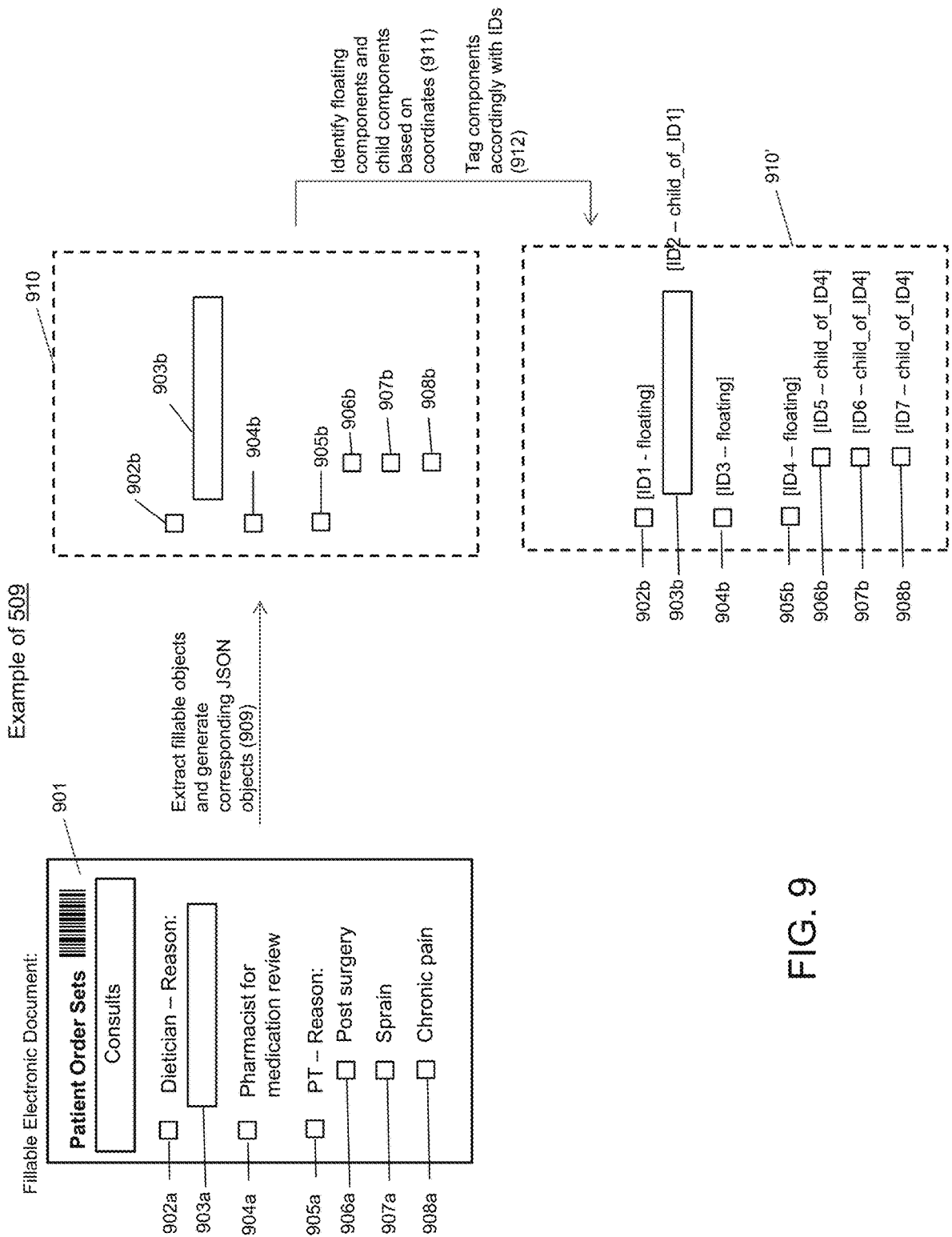
FIG. 9 is a flow diagram of an example computing process for identifying floating fillable web objects and child fillable web objects in a web form that has been generated from a FED.

Turning to FIG. 9, an example process is shown for identifying and tagging fillable objects in a web-based payload as a floating component or a child component. child component is one that is considered to be a subset of another fillable component.

Consider, for example, the FED 901 that includes fillable objects or fillable portions 902a, 903a, 904a, 905a, 906a, 907a and 908a. A check box (i.e. fillable portion 902a) is associated with a consult to see a dietician. In association with that check box 902a, a person is supposed to provide the reason for the dietician consult in the fillable box (i.e. fillable portion 903a) located below. In this case, the checkbox 902a is considered a floating component and the text box 903a is considered a child components of the checkbox 902a.

Similarly, if someone checks off the checkbox 905a to consult a physiotherapist or physical therapist, then the person is also expected to give a reason by selecting one of the reasons below (e.g. post surgery associated with the checkbox 906a, sprain associated with the checkbox 907a, and chronic pain associated with the checkbox 908a). These checkboxes 906a, 907a and 908a are considered child components of the checkbox 905a, and the checkbox 905a is considered a floating component.

At operation 909, the server 101 extracts the fillable objects or portions from the FED 901 and generates the corresponding JSON objects. The resulting JSON fillable objects are shown on a JSON page object 910, and are referenced by 902b, 903b, 904b, 905b, 906b, 907b and 908b.

At operation 911, the server 101 identifies the floating components and the child components in the page object 910 based on the coordinates, or more generally, their relative positions.

At operation 912, the server 101 tags components accordingly with IDs. A revised page object 910' shows the same fillable objects, but further including associated IDs that also identify whether the object is a floating component or a child component relative to another ID. For example, checkbox 902b is assigned ID1-floating, and the text box 903b is assigned ID2-child_of_ID1.

Figure 10:
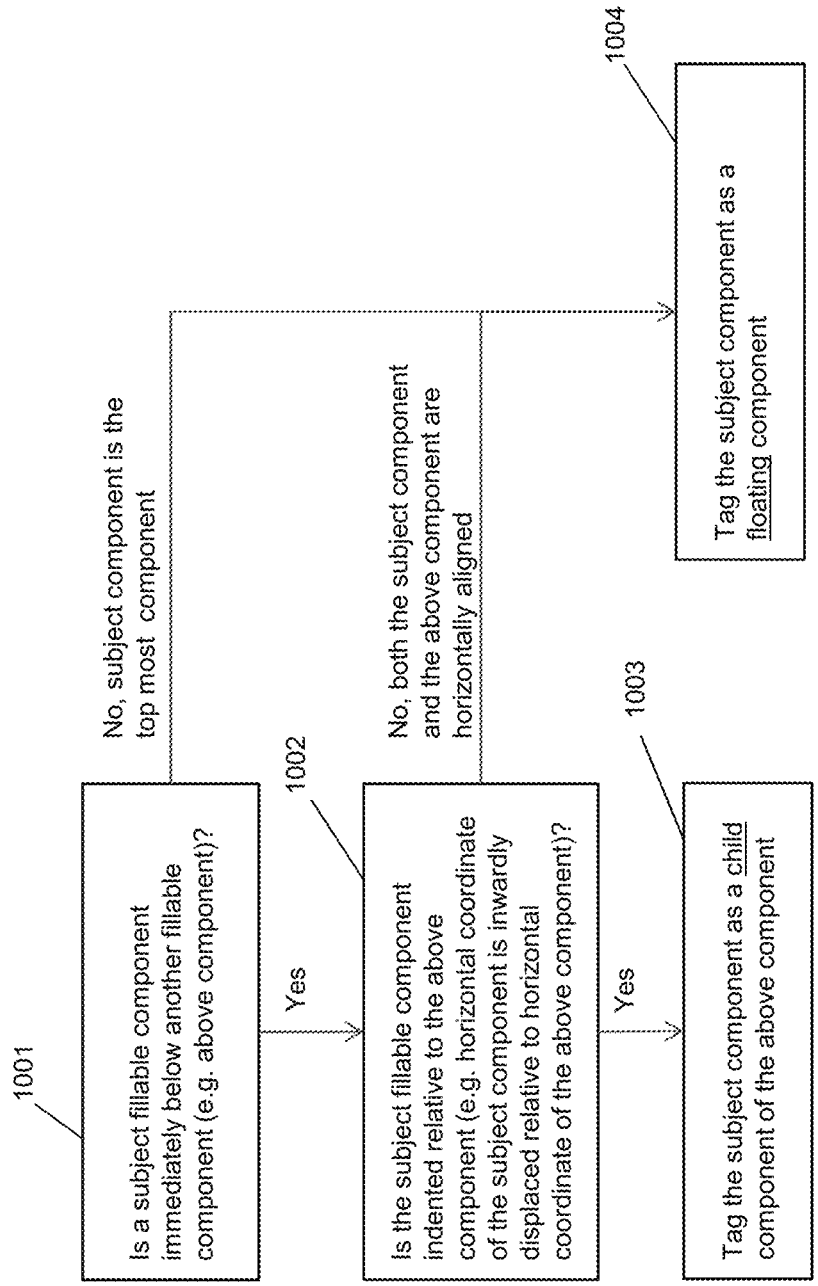
FIG. 10 is a flow diagram of example computer executable instructions for automatically determining whether a fillable web object is a floating component or a child component, according to an example aspect of an operation in FIG. 9.

Turning to FIG. 10, an example of executable instructions for implementing operation 911 is shown.

Block 1001: The server determines whether or not a subject fillable component is immediately below another fillable component (e.g. above component). If so, the process continues to block 1002.

Block 1002: The server determines whether or not the subject fillable component is indented relative to the above component (e.g. horizontal coordinate of the subject component is inwardly displaced relative to horizontal coordinate of the above component). If so, the process continues to block 1003.

Block 1003: The server tags the subject component as a child component of the above component.

If the condition at block 1001 is not true (e.g. the subject component is the top most component in the page), then the process continues to block 1004.

Likewise, if the condition at block 1002 is not true (e.g. both the subject component and the above component are horizontally aligned), then the process continues to block 1004.

Block 1004: The server tags the subject component as a floating component.

Figure 11:
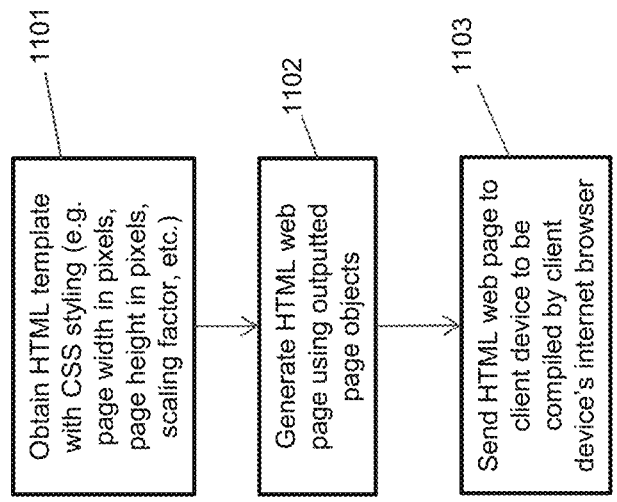
FIG. 11 is a flow diagram of example computer executable instructions for generating an HTML web page, according to an example aspect of an operation in FIG. 5.

Turning to FIG. 11, example executable instructions are provided generating an HTML webpage. These instructions, for example, could be used as part of implementing block 508.

Block 1101: The server 101 obtains a HTML template with CSS styling (e.g. page width in pixels, page height in pixels, scaling factor, etc.). This template, for example, is from the database 109.

Block 1102: The server generates the HTML web page using the HTML template and the outputted page objects (e.g. the web-based payload).

Block 1103: The server sends the HTML web page to the client device to be compiled by client device's Internet browser or app.

FIGS. 12 to 17b show executable instructions according to an example embodiment. The example is suitable for generating a web-based payload from a PDF document according the principles described above.

FIG. 12 shows a computation that converts PDF point coordinates to pixel coordinates based on the desired target_dpi of the web page. This process is used to help generate an image that has a resolution that is high enough so that the document does not look pixelated. Therefore, based on the target DPI, any given point in the PDF document is converted to a corresponding pixel.

Figure 13A:
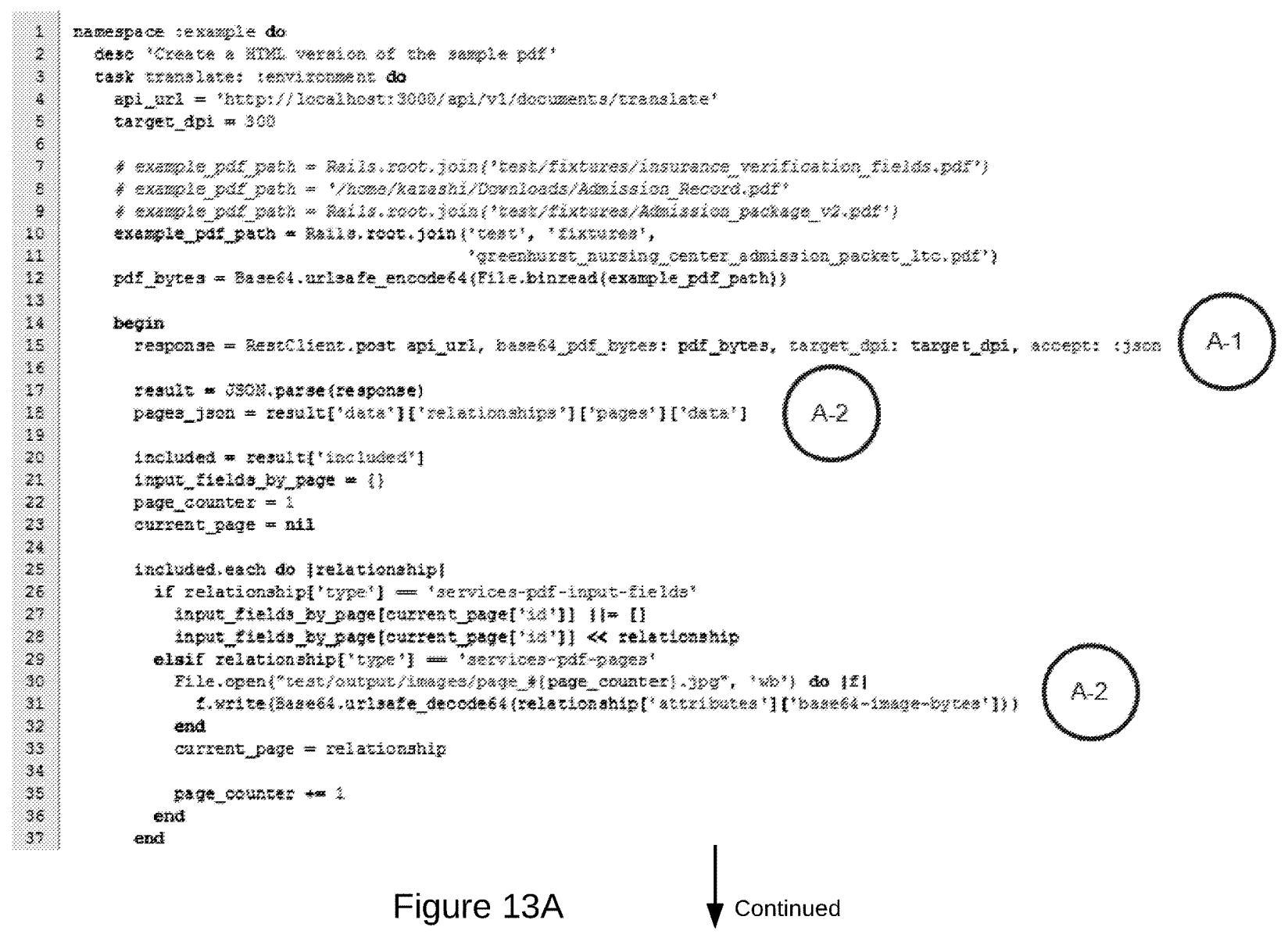

FIGS. 13A and 13B show a computation for converting the PDF document to the fillable web form, and that still looks like the PDF document.

A-1 shows executable instructions for reading in a fillable PDF document into the binary content and calls a local running REST service that will return or output the meta information about the PDF document. Representational state transfer (REST) or RESTful web services are a way of providing interoperability between computer systems on the Internet.

A-2 shows executable instructions for parsing the JSON response from the service and extracts out all of the input field by each page. The instructions also are for saving the image of the page to memory of the server.

A-3 shows executable instructions for saving the image of each page to a corresponding file called page_<num>.png. For example, page 1 would be named page_1.png.

A-4 shows executable instructions for generating a HTML page named index.html with all of input fields set, using a HTML template file with CSS styling. This is just an example of how the server can create a static HTML field from the data.

Figure 14A:
Figure 14B:
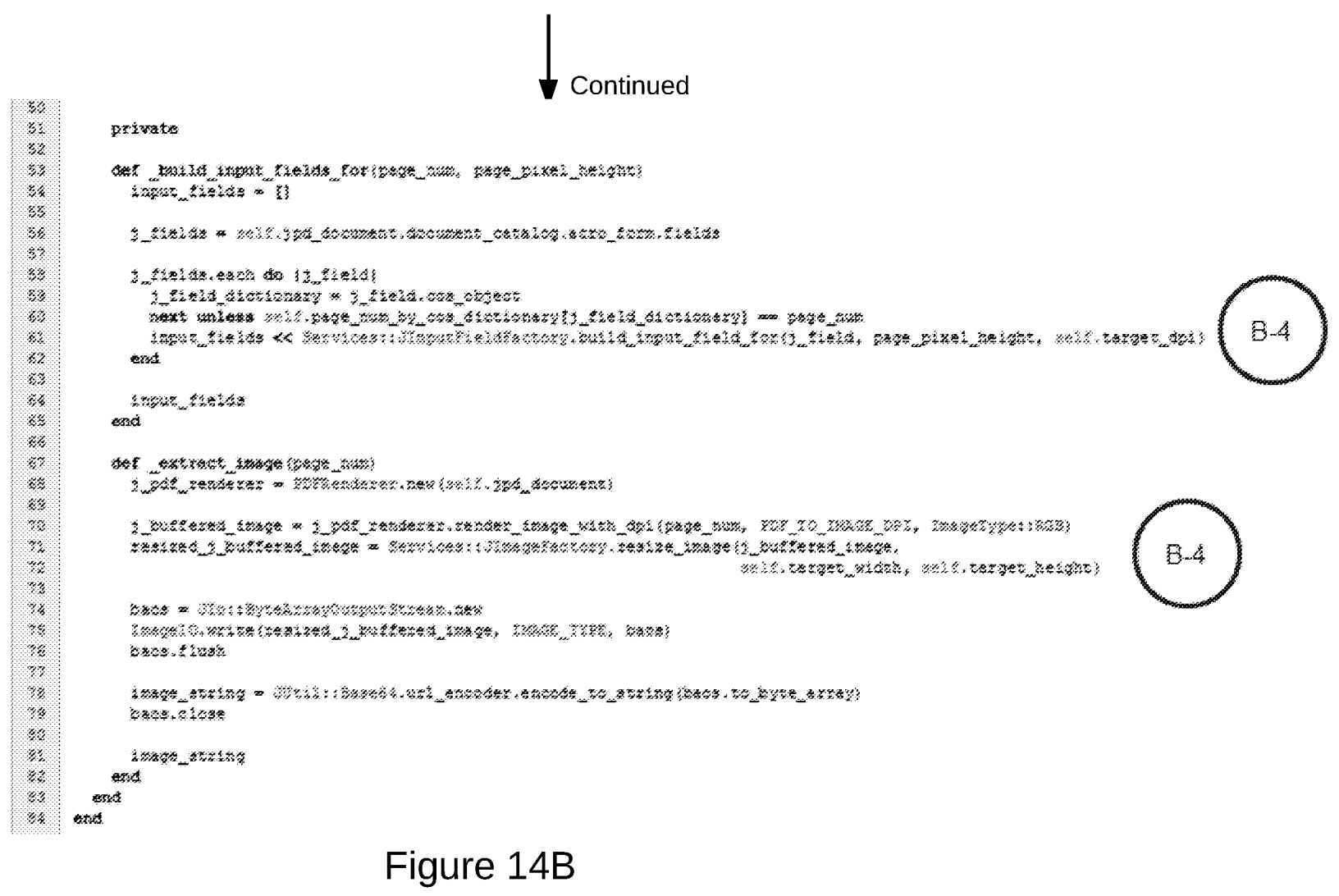

FIGS. 14A and 14B show further aspects of A-1.

B-1 shows calculating the width and the height of the page based on the DPI wanted.

B-2 shows extracting the background image for the page and returning it as a base64 encoded bytes. In an example aspect, this is easier to transmit between devices.

B-3 shows, that based on the requested width and height of the image, scaling it to the desired DPI.

B-4 shows calling another function to extract out all of the input fields out of the page and to return an InputField object (e.g. a fillable object).

B-5 shows generating a page object that represents the actual page with all of the InputFields (e.g. fillable objects) and the corresponding page image in base64 encoded bytes.

FIG. 15 shows further aspects of B-4.

In particular, C-1 shows computations for determining the top left point. C-2 shows computations for determining the bottom right point.

FIG. 16 shows how a program for designing forms, provided by Think Research Corporation, calls PDF Parser to generate a formdesigner document, a type of document provided by Think Research Corporation. In D-1, the instructions call PDF Parser with the desired width, height, and DPI for the images, and stores it in the context[:parsed_pdf_response] variable to be used by another function.

Figure 17B:
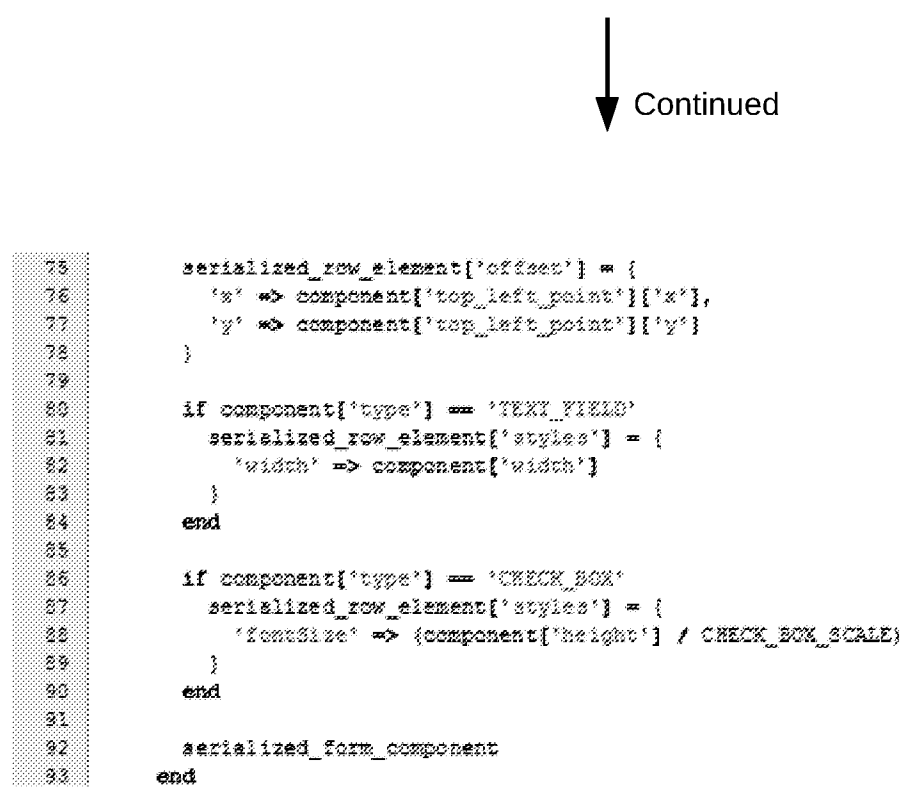

FIGS. 17A and 17B show the method set_floating_components using the context[parsed_pdf_document] and starts creating floating elements from it by calling the create_floating_component_object method with all of the information for that input field.

While many of the above examples relate to the JSON format for web-based structured objects, it is appreciated that other structured web-based formats are applicable to the principles described herein. For example, XML and YAML are other examples of structured data formats that could be used instead of JSON.

In the above examples, the server 101 obtains a FED from a user device and generates the corresponding fillable web form. However, in another example, a user device (e.g. has stored thereon a FED and locally executes the operations described herein to generate the corresponding fillable web form. More generally, a computing device, whether a user device or a server, can automatically generate the fillable web form using a FED. The same computing device, for example, can display the fillable web form, for example, via an Internet browser or an app.

Below are general example embodiments and their example aspects.

In a general example embodiment, a server system includes: a communication device in communication with a network and that receives a fillable electronic document (FED), the FED comprising a FED page, and the FED page comprising a fillable object that receives data; memory that store executable instructions for generating a web fillable form using the FED; and a processor that, responsive to receiving the FED, executes the executable instructions. The executable instructions comprise: identifying the fillable object and its respective location and size properties, the respective location and the size properties defined in a FED coordinate system; generating a web-based fillable object with location and size properties in a pixel coordinate system, which are derived from the location and the size properties defined in the FED coordinate system; generating a pixel image of the FED page; and generating a web object page that comprises the pixel image with the web-based fillable object overlaid the pixel image according to the location and size properties in the pixel coordinate system.

In an example aspect, the communication device is configured to receive the FED from a client device, and the executable instructions further include transmitting the web object page via the communication device to client device.

In another example aspect, the executable instructions for generating the pixel image of the FED page includes: generating an image of the FED page using meta data in the FED according to a given dots-per-inch (DPI); and converting the image to the pixel image.

In another example aspect, the fillable object in the FED is one of: a check box, a radial button, a text box, and a signature line.

In another example aspect, the FED page is one of multiple FED pages in the FED, and the executable instructions comprise generating a separate web object page corresponding to each one of the multiple FED pages.

In another example aspect, the executable instructions further include generating and outputting a HTML web page using the web object page and a HTML template, the HTML template comprising Cascade Sheet Style (CSS) data.

In another example aspect, the executable instructions further include computing a pixel width and a pixel height of the web object page based on: dimensions of the FED page and a desired dots-per-inch (DPI) value of the web page.

In another example aspect, generating the pixel image of the FED page includes: obtaining an image of the FED page, and rendering the pixel image using at least: the pixel width and the pixel height of the web object page, the desired DPI value, and the image of the FED page.

In another example aspect, the image is encoded as base64 bytes.

In another example aspect, the data received in the fillable object is biometric data.

In another example aspect, the FED page includes multiple fillable objects, and the executable instructions further include: generating multiple web-based fillable objects that are overlaid the pixel image; identifying which ones of the multiple web-based fillable objects are floating components and which other ones are child components based on relative positioning amongst the multiple web-based fillable objects; and tagging the multiple web-based fillable objects with IDs that indicate whether each one is a floating component or a child component.

In another example aspect, a given web-based fillable object is determined to be immediately below another given web-based fillable object and further determined to be indented relative to the another give web-based fillable object, and responsive to the determinations, the executable instructions comprise tagging the given web-based fillable object as the child component of the another given web-based fillable object.

In another example aspect, the FED is a Portable Document Format (PDF) document.

In another example aspect, the web object page is in a JavaScript Object Notation (JSON) format.

In another example aspect, the communication device is configured to receive multiple FEDs from multiple client devices, the server system generates multiple web object pages that respectively correspond to the multiple FEDs, and the communication device is configured to transmit the multiple web object pages to the respective multiple client devices.

In another general example embodiment, a computing system is provided and it includes: a user interface that receives a selection of a fillable electronic document (FED), the FED comprising a FED page, and the FED page comprising a fillable object that receives data; memory that at least stores the FED and executable instructions for generating a web fillable form using the FED; and a processor that, responsive to receiving the selection of the FED, executes the executable instructions. The executable instructions include: identifying the fillable object and its respective location and size properties, the respective location and the size properties defined in a FED coordinate system; generating a web-based fillable object with location and size properties in a pixel coordinate system, which are derived from the location and the size properties defined in the FED coordinate system; generating a pixel image of the FED page; and generating a web object page that comprises the pixel image with the web-based fillable object overlaid the pixel image according to the location and size properties in the pixel coordinate system. The computing system also includes a display device that displays a web-based form derived from the web object page.

In an example aspect, the memory further comprises an Internet browser, and the display device displays the web-based form within the Internet browser.

In another general example embodiment, one or more non-transitory computer readable storage mediums are provided. These one or more storage mediums store at least a fillable electronic document (FED) and instructions, the FED comprising a FED page, and the FED page comprising a fillable object that receives data. The instructions, when executed by a processor of a computing device, cause a computing device to at least: identify the fillable object and its respective location and size properties, the respective location and the size properties defined in a FED coordinate system; generate a web-based fillable object with location and size properties in a pixel coordinate system, which are derived from the location and the size properties defined in the FED coordinate system; generate a pixel image of the FED page; and generate a web object page that comprises the pixel image with the web-based fillable object overlaid the pixel image according to the location and size properties in the pixel coordinate system.

In another general example embodiment, a computing system is provided that includes: memory storing at least a fillable electronic document (FED), the FED comprising a FED page, and the FED page comprising a fillable object that receives data; and the memory further storing executable instructions for generating a web fillable form using the FED. The computing system also includes a processor that executes the executable instructions to at least: generate a web-fillable object corresponding to the fillable object in the FED page; generate a pixel image of the entire FED page; and generate the web fillable form comprising the pixel image and the web-fillable object overlaid the pixel image.

In another general example embodiment, one or more non-transitory computer readable storage mediums are provided that store at least a fillable electronic document (FED) and instructions. The FED includes a FED page, and the FED page includes a fillable object that receives data. The instructions, when executed by a processor of a computing device, cause a computing device to at least: generate a web-fillable object corresponding to the fillable object in the FED page; generate a pixel image of the entire FED page; and generate the web fillable form comprising the pixel image and the web-fillable object overlaid the pixel image.

It will be appreciated that the examples and corresponding diagrams used herein are for illustrative purposes only. Different configurations and terminology can be used without departing from the principles expressed herein. For instance, components and modules can be added, deleted, modified, or arranged with differing connections without departing from these principles.

It is also appreciated that the features described herein may be combined in different ways, even though those combinations are not explicitly described in the context of the example embodiments. The example embodiments are provided to convey the features in an example context, but other different combinations of the described features are also encompassed by the proposed systems and methods.

It will also be appreciated that any module or component exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the server system 101, the computing devices in communication thereto (e.g. devices 102, 114, 115, 116), or any component of or related to the server system 101, etc., or accessible or connectable thereto. Any application or module herein described may be implemented using computer readable/executable instructions that may be stored or otherwise held by such computer readable media.

Although the above principles have been described with reference to certain specific examples, various modifications thereof will be apparent to those skilled in the art as outlined in the appended claims.

The invention claimed is:

1. A server system for creating a web-based form from a fillable electronic document ("FED"), the server system comprising:
    a communication device in communication with a network and that receives the FED, the FED comprising a FED page, and the FED page comprising a FED fillable object that receives data;
    memory that stores executable instructions for generating a web fillable form using the FED;
    a processor that, responsive to receiving the FED, executes the executable instructions, which comprise:
        identifying the FED fillable object and its respective location and size properties, the respective location and the size properties defined in a FED coordinate system;
        generating a web-based fillable object with location and size properties in a pixel coordinate system, which are derived from the location and the size properties defined in the FED coordinate system, wherein the generating includes:
            identifying a point coordinate of a first diagonally opposite corner of the FED fillable object;
            converting the point coordinate of the first diagonally opposite corner to a pixel coordinate of a first diagonally opposite corner of the generated web-based fillable object;
            identifying a point coordinate of a second diagonally opposite corner of the FED fillable object;
            converting the point coordinate of the second diagonally opposite corner to a pixel coordinate of a second diagonally opposite corner of the generated web-based fillable object;
            storing the pixel coordinates of the first diagonally opposite corner and the second diagonally opposite corner in association with the web-based fillable object; and
            using the pixel coordinates to define the location and the size of the web-based fillable object;
        determining whether the web-based fillable object is a child web-based fillable object or a floating web-based fillable object by determining whether a horizontal coordinate of the web-based fillable object is inwardly displaced relative to a horizontal coordinate of a second web-based fillable object, the second web-based fillable object above the web-based fillable object, and tagging the web-based fillable object as either a child web-based fillable object or a floating web-based fillable object based on the determination, and wherein the tagging indicates whether the web-based fillable object is a subset of another web-based fillable object;
generating a pixel image of the FED page; and
generating a web object page that comprises the pixel image with the web-based fillable object overlaid the pixel image according to the location and size properties in the pixel coordinate system.

2. The server system of claim 1 wherein the communication device is configured to receive the FED from a client device, and the executable instructions further comprise transmitting the web object page via the communication device to client device.

3. The server system of claim 1 wherein the FED fillable object in the FED is one of: a check box, a radial button, a text box, and a signature line.

4. The server system of claim 1 wherein the FED page is one of multiple FED pages in the FED, and the executable instructions comprise generating a separate web object page corresponding to each one of the multiple FED pages.

5. The server system of claim 1 wherein the executable instructions for generating the pixel image of the FED page comprises: generating an image of the FED page according to a given dots-per-inch (DPI); and converting the image to the pixel image.

6. The server system of claim 1 wherein the executable instructions further comprise generating and outputting a hypertext text markup language (HTML) web page using the web object page and a HTML template, the HTML template comprising Cascade Sheet Style (CSS) data.

7. The server system of claim 1 wherein the executable instructions further comprise computing a pixel width and a pixel height of the web object page based on: dimensions of the FED page and a desired dots-per-inch (DPI) value of the web page.

8. The server system of claim 7 wherein generating the pixel image of the FED page comprises: obtaining an image of the FED page rendered according to the desired DPI value, and rendering the pixel image using at least: the pixel width and the pixel height of the web object page, the desired DPI value, and the image of the FED page.

9. The server system of claim 1 wherein the pixel image is encoded as base64 bytes.

10. The server system of claim 1 wherein the data received in the FED fillable object is biometric data.

11. The server system of claim 1 wherein the FED page comprises multiple fillable objects, and the executable instructions further comprise: generating multiple web-based fillable objects that are overlaid the pixel image; identifying which ones of the multiple web-based fillable objects are floating components and which other ones are child components based on relative positioning amongst the multiple web-based fillable objects; and tagging the multiple web-based fillable objects with IDs that indicate whether each one is a floating component or a child component.

12. The server system of claim 1 wherein a given web-based fillable object is determined to be immediately below another given web-based fillable object and further determined to be indented relative to the another give web-based fillable object, and responsive to the determinations, the executable instructions comprise tagging the given web-based fillable object as the child component of the another given web-based fillable object.

13. The server system of claim 1 wherein tagging the web-based fillable object as a child web-based fillable object includes generating a tag that includes a reference to the second web-based fillable object.

14. The server system of claim 1 wherein the web object page is in a JavaScript Object Notation (JSON) format.

15. The server system of claim 1 wherein the communication device is configured to receive multiple FEDs from multiple client devices, the server system generates multiple web object pages that respectively correspond to the multiple FEDs, and the communication device is configured to transmit the multiple web object pages to the respective multiple client devices.

16. A computing system for creating a web-based form from a fillable electronic document ("FED"), the system comprising:
a user device that receives a selection of the FED, the FED comprising a FED page, and the FED page comprising a FED fillable object that receives data;
memory that at least stores the FED and executable instructions for generating a web fillable form using the FED;
a processor that, responsive to receiving the selection of the FED, executes the executable instructions, which comprise:
identifying the FED fillable object and its respective location and size properties, the respective location and the size properties defined in a FED coordinate system;
generating a web-based fillable object with location and size properties in a pixel coordinate system, which are derived from the location and the size properties defined in the FED coordinate system, wherein the generating includes:
identifying a point coordinate of a first diagonally opposite corner of the FED fillable object;
converting the point coordinate of the first diagonally opposite corner to a pixel coordinate of a first diagonally opposite corner of the generated web-based fillable object;
identifying a point coordinate of a second diagonally opposite corner of the FED fillable object;
converting the point coordinate of the second diagonally opposite corner to a pixel coordinate of a second diagonally opposite corner of the generated web-based fillable object; and
storing the pixel coordinates of the first diagonally opposite corner and the second diagonally opposite corner in association with the web-based fillable object, and using the pixel coordinates to define the location and the size of the web-based fillable object;
determining whether the web-based fillable object is a child web-based fillable object or a floating web-based fillable object by determining whether a horizontal coordinate of the web-based fillable object is inwardly displaced relative to a horizontal coordinate of a second web-based fillable object, the second web-based fillable object above the web-based fillable object, and tagging the web-based fillable object as a child component or a floating component based on the determination, and wherein the tagging indicates whether the web-based fillable object is a subset of another web-based fillable object;
generating a pixel image of the FED page; and
generating a web object page that comprises the pixel image with the web-based fillable object overlaid the pixel image according to the location and size properties in the pixel coordinate system; and
a display device that displays the web-based form derived from the web object page.

17. The computing system of claim 16, wherein the memory further comprises an Internet browser, and the display device displays the web-based form within the Internet browser.

18. One or more non-transitory computer readable storage mediums that store at least a fillable electronic document (FED) and instructions, the FED comprising a FED page, and the FED page comprising FED a fillable object that receives data; and the instructions, when executed by a processor of a computing device, cause a computing device to at least:
identify the FED fillable object and its respective location and size properties, the respective location and the size properties defined in a FED coordinate system;
generate a web-based fillable object with location and size properties in a pixel coordinate system, which are derived from the location and the size properties defined in the FED coordinate system, wherein the generating includes:
identifying a point coordinate of a first diagonally opposite corner of the FED fillable object;
converting the point coordinate of the first diagonally opposite corner to a pixel coordinate of a first diagonally opposite corner of the generated web-based fillable object;
identifying a point coordinate of a second diagonally opposite corner of the FED fillable object; converting the point coordinate of the second diagonally opposite corner to a pixel coordinate of a second diagonally opposite corner of the generated web-based fillable object;
storing the pixel coordinates of the first diagonally opposite corner and the second diagonally opposite corner in association with the web-based fillable object, and using the pixel coordinates to define the location and the size of the web-based fillable object;
determine whether the web-based fillable object is a child web-based fillable object or a floating web-based fillable object by determining whether a horizontal coordinate of the web-based fillable object is inwardly displaced relative to a horizontal coordinate of a second web-based fillable object, the second web-based fillable object above the web-based fillable object, and tag the web-based fillable object as either a child component or a floating component based on the determination, and wherein the tagging indicates whether the web-based fillable object is a subset of another web-based fillable object;
generate a pixel image of the FED page; and
generate a web object page that comprises the pixel image with the web-based fillable object overlaid the pixel image according to the location and size properties in the pixel coordinate system.

19. A computing system for creating a web-based form from a fillable electronic document ("FED"), the system comprising:
memory storing at least the FED, the FED comprising a FED page, and the FED page comprising a FED fillable object that receives data;
the memory further storing executable instructions for generating a web fillable form using the FED;
a processor that executes the executable instructions to at least:
generate a web-based fillable object corresponding to the FED fillable object in the FED page, wherein the generating includes:
identifying a point coordinate of a first diagonally opposite corner of the FED fillable object; converting the point coordinate of the first diagonally opposite corner to a pixel coordinate of a first diagonally opposite corner of the generated web-based fillable object;
identifying a point coordinate of a second diagonally opposite corner of the FED fillable object;
converting the point coordinate of the second diagonally opposite corner to a pixel coordinate of a second diagonally opposite corner of the generated web-based fillable object;
storing the pixel coordinates of the first diagonally opposite corner and the second diagonally opposite corner in association with the web-based fillable object, and using the pixel coordinates to define the location and the size of the web-based fillable object;
determine whether the web-based fillable object is a child web-based fillable object or a floating web-based fillable object by determining whether a horizontal coordinate of the web-based fillable object is inwardly displaced relative to a horizontal coordinate of a second web-based fillable object, the second web-based fillable object above the web-based fillable object, and tag the web-based fillable object as either a child web-based fillable object or a floating web-based fillable object based on the determination, and wherein the tagging indicates whether the web-based fillable object is a subset of another we-based fillable object;
generate a pixel image of the entire FED page; and
generate the web fillable form comprising the pixel image and the web-fillable object overlaid the pixel image.

20. One or more non-transitory computer readable storage mediums that store at least a fillable electronic document (FED) and instructions, the FED comprising a FED page, and the FED page comprising a FED fillable object that receives data; and the instructions, when executed by a processor of a computing device, cause a computing device to at least:
generate a web-based fillable object corresponding to the FED fillable object in the FED page, wherein the generating includes:
identifying a point coordinate of a first diagonally opposite corner of the FED fillable object;
converting the point coordinate of the first diagonally opposite corner to a pixel coordinate of a first diagonally opposite corner of the generated web-based fillable object;
identifying a point coordinate of a second diagonally opposite corner of the FED fillable object;
converting the point coordinate of the second diagonally opposite corner to a pixel coordinate of a second diagonally opposite corner of the generated web-based fillable object;
storing the pixel coordinates of the first diagonally opposite corner and the second diagonally opposite corner in association with the web-based fillable object, and using the pixel coordinates to define the location and the size of the web-based fillable object;
determine whether the web-based fillable object is a child web-based fillable object or a floating web-based fillable object by determining whether a horizontal coordinate of the web-based fillable object is inwardly displaced relative to a horizontal coordinate of a second web-based fillable object, the second web-based fillable object above the web-based fillable object, and tag the web-based fillable object as either a child web-based fillable object or a floating web-based fillable object based on the determination, and wherein the tagging indicates whether the web-based fillable object is a subset of another web-based fillable object;

generate a pixel image of the entire FED page; and generate the web fillable form comprising the pixel image and the web-fillable object overlaid the pixel image.

* * * * *